(12) United States Patent
Palangetic et al.

(10) Patent No.: US 11,890,383 B2
(45) Date of Patent: *Feb. 6, 2024

(54) CAPSULES WITH OPACIFIER

(71) Applicant: Capsugel Belgium NV, Bornem (BE)

(72) Inventors: Ljiljana Palangetic, Colmar (FR); Delphine Nombret, Heidolsheim (FR); Stefaan Jaak Vanquickenborne, Rijmenam (BE)

(73) Assignee: Capsugel Belgium NV, Bornem (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/978,780

(22) Filed: Nov. 1, 2022

(65) Prior Publication Data

US 2023/0090812 A1 Mar. 23, 2023

Related U.S. Application Data

(63) Continuation of application No. 17/046,132, filed as application No. PCT/EP2019/062360 on May 14, 2019, now Pat. No. 11,517,535.

(30) Foreign Application Priority Data

May 14, 2018 (EP) ..................... 18172133

(51) Int. Cl.
*A61K 9/48* (2006.01)
(52) U.S. Cl.
CPC .......... *A61K 9/4825* (2013.01); *A61K 9/4808* (2013.01); *A61K 9/4833* (2013.01)
(58) Field of Classification Search
CPC ... A61K 9/4825; A61K 9/4808; A61K 9/4833
See application file for complete search history.

(56) References Cited

U.S. PATENT DOCUMENTS

| | | | |
|---|---|---|---|
| 3,784,684 | A | 1/1974 | Bossert et al. |
| 4,993,137 | A | 2/1991 | Muto et al. |
| 6,071,536 | A | 6/2000 | Suzuki et al. |
| 6,790,495 | B1 | 9/2004 | Tomka et al. |
| 2005/0214361 | A1 | 9/2005 | Mizutani et al. |
| 2009/0010975 | A1 | 1/2009 | Shiraishi |
| 2019/0105278 | A1 | 4/2019 | Wätzig et al. |
| 2020/0187538 | A1 | 6/2020 | Budde et al. |

FOREIGN PATENT DOCUMENTS

| | | |
|---|---|---|
| CA | 3100248 A1 | 11/2019 |
| CN | 101961346 A | 2/2011 |
| CN | 102295788 A | 12/2011 |
| CN | 105395513 A | 3/2016 |
| CN | 105796803 A | 7/2016 |
| CN | 106135153 A | 11/2016 |
| CN | 112118835 A | 12/2020 |
| EP | 3400810 A1 | 11/2018 |
| EP | 3758685 A1 | 1/2021 |
| JP | S48-028621 A | 4/1973 |
| JP | S61100516 A | 5/1986 |
| JP | H7-124462 A | 5/1995 |
| JP | H11-292791 A | 10/1999 |
| JP | 2003-300872 A | 10/2003 |
| JP | 2007-284394 A | 11/2007 |
| JP | 2010-174043 A | 8/2010 |
| JP | 2013-515715 A | 5/2013 |
| JP | 2019-515917 A | 6/2019 |
| WO | WO 96/29996 A1 | 10/1996 |
| WO | WO 01/07507 A1 | 2/2001 |
| WO | WO 2011/080647 A2 | 7/2011 |
| WO | WO 2017/182350 A1 | 10/2017 |
| WO | WO 2019/219693 A1 | 11/2019 |

OTHER PUBLICATIONS

Communication of a Notice of Opposition, dated May 20, 2022, issued in corresponding European Application No. 19721509.8, 26 pages.
Communication, issued by the International Bureau of WIPO in PCT/EP2020/078280, dated Mar. 8, 2022, regarding Third Party Observation dated Feb. 9, 2022, with English-language translation ,23 pages.
International Preliminary Examination Report for PCT/EP2019/062360, dated Sep. 8, 2020.
International Search Report and Written Opinion for PCT/EP2019/062360, dated Aug. 23, 2019.
International Search Report and Written Opinion, dated Jan. 25, 2021, issued in PCT/EP2020/078280, 11 pages.
Podczeck and Jones, "Manufacture and properties of two-piece hard capsules," *Pharmaceutical Capsules, Second Edition*, Pharmaceutical Press, 2004, pp. 79-82, 5 pages.
Sato et al., "Discrimination Between Natural Calcium Carbonate and Synthetic Calcium Carbonate," *Japanese Central Customs Laboratory Report*, Dec. 2019, 12 pages, and English-language translation, 22 pages.
Sheskey et al., *Handbook of Pharmaceutical Excipients*, Pharmaceutical Press, 2017, pp. 138-139, 5 pages.
Wikipedia, "Differences Between Versions of Calcium Carbonate," URL: https://ja.wikipedia.org/w/index.php?title=%E7%82%AD%E9%85%B8%E3%82%AB%E3%83%AB%E3%82%B7%E3%82%A6%E3%83%A0&diff=74022621&oldid=74021348, dated Aug. 28, 2019, 6 pages, and English-language translation.
Office Action, dated Apr. 11, 2023, issued in related Japan Application No. 2020-564215 (w/English-language Translation). 6 pages.
Brief Communication (Oral Proceedings European Patent No. 3758685B1), dated Jul. 28, 2023, 11 pages.
"D13: Comparative examples," submitted with Reply to Communication of a Notice of Opposition dated Sep. 26, 2022, 2 pages.

(Continued)

*Primary Examiner* — Robert A Wax
*Assistant Examiner* — Olga V. Tcherkasskaya
(74) *Attorney, Agent, or Firm* — Klarquist Sparkman, LLP (57) ABSTRACT

The present invention provides ingestible dosage form articles such as opaque capsules with reduced light transmittance.

18 Claims, 1 Drawing Sheet

(56) References Cited

OTHER PUBLICATIONS

Information sheet of Cal-Carb 0 ground calcium carbonate cited in point 2 of "Handbook of Pharmaceutical Excipients," $8^{th}$ ed., 2017; excerpt, date unknown, 4 pages.
Information sheet of Cal-Carb 325 ground calcium carbonate cited in point 2 of "Handbook of Pharmaceutical Excipients," $8^{th}$ ed., 2017; excerpt, date unknown, 4 pages.
Information sheet of Calcipress™ calcium carbonate 90S cited in point 2 of "Handbook of Pharmaceutical Excipients," $8^{th}$ ed., 2017; excerpt, Particle Dynamics, Sep. 2018, 1 page.
Information sheet of DESTAB™ calcium carbonate 90SE cited in point 2 "Handbook of Pharmaceutical Excipients," $8^{th}$ ed., 2017; excerpt, Particle Dynamics, 2022, 5 pages.
Information sheet of E170 Calcium carbonate, cited in point 2 of "Handbook of Pharmaceutical Excipients," $8^{th}$ ed., 2017; excerpt, Sep. 5, 2021, 2 pages.
Information sheet of MagGran® granulates cited in point 2 of "Handbook of Pharmaceutical Excipients," $8^{th}$ ed., 2017; excerpt, Pharmaceutical Networking, Sep. 22, 2014, 8 pages.
Reply to Communication of a Notice of Opposition, (Opposition against European Patent No. EP3758685B1), Sep. 26, 2022, 12 pages.
Reply to Summons to Attend Oral Proceedings (Opposition against European Patent No. EP3758685B1), Jul. 26, 2023, 6 pages.
Safety data sheet of Precipitated Calcium Carbonate cited in point 2 of "Handbook of Pharmaceutical Excipients," $8^{th}$ ed., 2017; excerpt, Minerals Technologies, Jan. 12, 2009; Revision Date: Jul. 23, 2019, 9 pages.
Specification of Magnesia 452 calcium carbonate, Magnesia Mineral Compounds, Dec. 7, 2017, 2 pages.
Summons to Attend Oral Proceedings Pursuant to Rule 115(1) EPC, European Patent No. 3758685B1, Oct. 31, 2022, 25 pages.

FIG. 1A

FIG. 1B

CAPSULES WITH OPACIFIER

CROSS REFERENCE TO RELATED APPLICATIONS

This application is a continuation of U.S. application Ser. No. 17/046,132, filed on Oct. 8, 2020, which is the U.S. National Stage of International Application No. PCT/EP2019/062360, filed May 14, 2019, which was published in English under PCT Article 21(2), which in turn claims the benefit of European Application No. EP 18172133.3, filed May 14, 2018, each of which is herein incorporated by reference in its entirety.

TECHNICAL FIELD

The present disclosure relates to formulations for the production of opaque capsules or capsule shells and opaque capsules made therefrom. Said capsules shield the ingredient inside from light, while retaining good mechanical properties. The invention also relates to methods for making such capsules and the use thereof for delivery of the ingredients.

BACKGROUND OF THE INVENTION

Certain medicaments or other active ingredients such as nutraceutical etc. are sensitive to degradation by light and need to be stored in a light-shielded manner. Within capsules, the opacity of the capsule hence regulates the light-shielding. Typically in the prior art, titanium-dioxide ($TiO_2$) is used for creating opacity in the capsule shells.

Driven by the continuous search for new products, replacements of the well-known opacifier were sought.

There are many opacifiers, but due to their limited opacifying capacity, not all of them will give the capsules with good light blocking properties while maintaining the mechanical strength required for producing, processing and filling with active ingredient.

$CaCO_3$ is defined as one of many potential opacifiers, light blocking agents, light-shielding materials or pigments in a number of patents or patent applications such as: EP1580229A1, WO2011143347, WO2015174868A1, EP1502588A1, U.S. Pat. No. 3,784,684, EP1757275A1, JP2003300872A, US200244970A1, and US20100021535A1. However, none of these documents has documented experimental success with $CaCO_3$ in term of obtaining both an opacifying effect and retaining mechanical strength of capsules, when incorporating the $CaCO_3$ in the capsule formulation itself rather than applying it in some sort of coating on a capsule shell support. EP1574220A1 discloses the use of calcium lactate as an opacifier in hydroxypopylmethylcellulose (HPMC)-based capsules. Said calcium lactate however has a rather low refractive index and hence does not result in sufficient opacity. No information is given on the mechanical strength of such capsules.

Accordingly, it is an object of the present invention to provide capsules with light-shielding capacity, without the need of using $TiO_2$, and still remaining good mechanical properties.

SUMMARY

The present invention relates to capsule shell formulation design focusing on the selection of opacifiers that reduce the light transmittance of capsules while retaining the mechanical stability needed for producing, storing, processing, filling etc. of said capsules.

The inventors have established that calcium carbonate ($CaCO_3$), when present in a specific concentration range provided the best balance between good opacity and good mechanical properties, i.e. on the opacifying level and on the mechanical strength level for capsules.

This was unexpected, since numerous publications have been reporting on the potential use of calcium carbonate as opacifier, however without showing actual results on both opacity and mechanical strength, when the opacifier is mixed within the capsule forming formulation.

Having conducted extensive research on the matter, the inventors now put forward the following aspects of the invention:

Aspect 1. A capsule forming composition comprising:
a film forming agent selected from the group consisting of: gelatin, polysaccharides, modified starches, cellulose derivatives or synthetic polymers or a combination thereof; and
an opacifying agent in the form of calcium carbonate, preferably precipitated calcium carbonate, in an amount of between 3 and 10 wt % based on dry weight of the capsule forming formulation.

Aspect 2. The capsule forming composition according to aspect 1, wherein said opacifying agent is present in an amount of between 4 and 8 wt %, more preferably of between 5 and 7 wt %, such as from 4.5 to 6.5 wt % based on dry weight of the capsule forming formulation.

Aspect 3. The capsule forming composition according to aspect 1 or 2, wherein said calcium carbonate has a substantially round or prismatic particle shape. In a particular embodiment, the calcium carbonate encompasses small round or prismatic uniform particles.

Aspect 4. The capsule forming composition according to any one of aspects 1 to 3, wherein said $CaCO_3$ has a median particle size of between 0.2 and 2.0 µm or a. D4,3 particle size of about 10 µm or less.

The average particle size can be expressed as a "D50" (Dv50) median particle size of between 0.2 to 2 µm, such as between 0.5 and 1.5 µm, more preferably of between 0.3 to 1.2 µm, more preferably of between 0.4 to 1.1 µm, such as about 1 µm.

Alternatively, the particles can have a "D4,3" particle size of about 10 µm or less, more preferably of about 8 µm or less, such as about 6 µm or less, or about 4 µm or less, more particularly of between 1 and 10 µm, or between 1 and 8 µm, preferably of between 2 and 6 µm, more preferably of about 4 µm, e.g. between 3.5 and 4.5 µm.

In one embodiment, the particle size distribution, defined as particle size span, which is as low as possible. Preferably, said span is lower than 15, such as lower than 10, preferably below 8, more preferably below 6.

Aspect 5. The capsule forming composition according to any one of aspects 1 to 4, having a calcium carbonate concentration of about 10%, typically will have an opacity coefficient of 20% or higher. The capsule forming composition according to any one of aspects 1 to 4, having a calcium carbonate concentration of about 5%, typically will have an opacity coefficient of 15% or higher. Alternatively, capsule forming composition according to any one of aspects 1 to 4 has a light transmittance at 650 nm of 35% or lower when the capsule comprises 10% calcium carbonate or a light transmittance at 650 nm of 55% or lower when the capsule comprises 5% calcium carbonate.

Aspect 6. The capsule forming composition according to any one of aspects 1 to 5, wherein said calcium carbonate is in the form of precipitated calcium carbonate.

Aspect 7. The capsule forming composition according to any one of aspects 1 to 6, wherein said film-forming agent is a cellulose based polymer such as methylcellulose, hydroxymethylcellulose, hydroxypropylcellulose, methylhydroxyethylcellulose, hydroxypropylmethylcellulose, hydroxypropylmethylcellulose phthalate, hydroxypropylmethylcellulose acetate succinate, carboxymethylethylcellulose or a combination thereof, preferably hydroxypropylmethylcellulose.

Aspect 8. The capsule forming composition according to any one of aspects 1 to 6, wherein said film-forming agent is a synthetic polymer such as polyvinyl alcohol, polyethylene glycol/oxide, polyvinyl acetate, polyacrylamide, polyvinylacetal diethylamino acetate, aminoalkylmethacrylate copolymer E, polyvinylpyrolidone, or a combination thereof.

Aspect 9. The capsule forming composition according to any one of aspects 1 to 6, wherein said film-forming agent is polypeptide- (protein-) based polymer such as gelatin, collagen, zein, casein, soy protein, or mung bean protein, whey protein, pea protein.

Aspect 10. The capsule forming composition according to any one of aspects 1 to 6, wherein said film-forming agent is a polysaccharide, preferably pullulan, starch, cellulose, or dextran.

Aspect 11. The capsule forming composition according to any one of aspects 1 to 6, wherein said film-forming agent is an acrylate and/or (meth)acrylate based polymer such as ethyl acrylate-methyl methacrylate copolymer, polyacrylic acid, or polymethyl methacrylate.

Aspect 12. The capsule forming composition according to any one of aspects 1 to 11, further comprising one or more additives such as: gelling agents, gelling aids, viscosity modifiers, de-foaming aids, plasticizers, lubricants, colorants, solvents, solvent aids, surfactants, dispersants, solubilizers, stabilizers, correctives, sweeteners, adsorbents, adherent's, antioxidants, antiseptics, preservatives, desiccants, flavors, perfumes, anti-oxidants, pH adjusters, binders, disintegrating agents, release-controlling agents.

Aspect 13. A capsule formed from the capsule forming composition according to any one of aspects 1 to 12.

Preferably, said capsule comprises:
   a film forming agent selected from the group consisting of: gelatin, polysaccharides, modified starches, cellulose derivatives, or synthetic polymers; and
   an opacifying agent in the form of calcium carbonate in an amount of between 3 and 10 wt % based on dry weight of the capsule forming composition, preferably in an amount of between 4 and 8 wt %, more preferably of between 5 and 7 wt %, such as from 4.5 to 6.5 wt % based on dry weight of the capsule forming composition.

In a preferred embodiment, when said capsule comprises HPMC as film-forming agent, the final capsule will comprise from 4 to 6 wt. % water based on the total capsule weight. In a further preferred embodiment, when said capsule comprises gelatin as film-forming agent the final capsule will comprise from 12 to 15 wt. % of water based on the total capsule weight. These concentrations are based on ambient temperature and humidity (25° C. (+/−2° C.) and RH of 30-50%).

Aspect 14. The capsule according to aspect 13, which is a hard shell capsule, preferably a gelatin, pullulan or HPMC based hard shell capsule.

Aspect 15. A method of producing a capsule with reduced light transmittance (also called opaque capsules), comprising providing the film-forming composition according to any one of claims 1 to 12, and forming capsules using a dip coating process.

Aspect 16. A method of preparing a film-forming composition according to any one of aspects 1 to 12, comprising the steps of:
   a) preparing an aqueous dispersion of calcium carbonate opacifier, through mixing;
   b) preparing a film-forming formulation comprising one or more film-forming agent selected from the group of: gelatin, polysaccharides, modified starches, cellulose derivatives or synthetic polymers or a combination thereof;
   c) adding the aqueous dispersion of step a) to the solution of step b); and
   d) mixing the resulting dispersion of step c), thereby obtaining the film forming composition, comprising between 3 and 10 wt %, preferably of between 4 and 8 wt %, more preferably of between 5 and 7 wt %, such as from 4.5 to 6.5 wt % $CaCO_3$ based on final dry weight of the film-forming composition. In one embodiment, said film-forming composition comprises 15-25 wt % HPMC such as 20.5 wt % HPMC; or 25-35 wt %, such as about 31 wt % gelatin based on total dry weight of final capsule forming formulation.

Aspect 17. The method according to aspect 16, wherein step c) is performed in two steps: c1) adding a part of the film-forming formulation of step b) to the dispersion of step a) to form a slurry and c2), adding said slurry to the remaining film forming formulation. Preferably, said slurry is formed using high shear mixing such as mixing at a speed of at least 10000 rpm, such as e.g. 12000 rpm or more for at least 2 minutes.

Aspect 18. The method according to aspect 16 or 17, wherein said mixing in step a) encompasses high shear mixing, such as mixing at a speed of at least 15000 rpm, preferably at least 20000 rpm for at least 4 minutes.

Aspect 19. The method according to any one of aspect 16 to 18, wherein the film-forming agent comprises gelatin, pullulan, hydroxypopylmethylcellulose acetate succinate (HPMCAS) or HPMC.

Additionally, the film-forming solution further comprises one or more additives such as: gelling agents, gelling aids, viscosity modifiers, de-foaming aids, plasticizers, lubricants, colorants, solvents, solvent aids, surfactants, dispersants, solubilizers, stabilizers, correctives, sweeteners, adsorbents, adherent's, antioxidants, antiseptics, preservatives, desiccants, flavors, perfumes, anti-oxidants, pH adjusters, binders, disintegrating agents, release-controlling agents.

Aspect 20. The method according to any one of aspects 16 to 19, wherein the opacifier is present in an amount of between 4 and 8 wt %, more preferably of between 5 and 7 wt % based on final dry weight of the film-forming composition.

Aspect 21. A method of making capsules comprising the steps of:
   a) preparing a film forming composition according to the method of any one of aspects 16 to 20 and
   b) producing a capsule by means of dip molding. Typically, such a dip molding method comprises the steps of: dipping a mold pin in the film-forming composition at an adequate temperature to allow film-forming thereof on said dipping pin; (air-)drying said film on the dipping pin; and removing the film-formed capsule half from said dipping pin.

Aspect 22. The capsule according to aspect 13 or 14, or the capsule obtained by the method of aspect 21, wherein:
  when the capsule is an HPMC capsule having a calcium carbonate concentration of about 5 or 10%, it typically will have an opacity coefficient of 20% or higher. An HPMC capsule with 5% $CaCO_3$ will typically have a light transmittance at 650 nm of 35% or lower, while an HPMC capsule having about 10% $CaCO_3$ typically will have a light transmittance at 650 nm of 10% or lower.
  when the capsule is a gelatin (HGC) capsule having a calcium carbonate concentration of about 5 or 10%, it typically will have an opacity coefficient of 17% or higher. An HGC capsule with 10% $CaCO_3$ will typically have a light transmittance at 650 nm of 30% or lower, while an HGC capsule having about 5% $CaCO_3$ typically will have a light transmittance at 650 nm of 55% or lower.

These values are determined on the average capsule wall thickness of standard capsules, i.e. of about 100 μm.

Aspect 23. The capsule according to aspect 22, filled with a filling formulation comprising an active ingredient such as a nutrient or a medicament.

Aspect 24. The capsule according to aspect 23, wherein the active ingredient is present in an amount ranging from about 0.05 wt % to about 100 wt % based on the total dry weight of said filling formulation. Typically, the active ingredient can present in an amount ranging from about 0.5 wt % to about 90 wt % based on the total dry weight of said filling formulation, preferably from about 1 wt % to about 50 wt %, more preferably from about 5 wt % to about 30 wt % based on the total weight of said filling formulation Aspect 25. The capsule according to any of aspects 23 or 24, wherein the active ingredient is an active pharmaceutical ingredient, nutritional supplement, nutraceutical, vitamin, mineral, cosmetic, health food, preferably a light unstable active ingredient.

DETAILED DESCRIPTION OF THE INVENTION

Development of dosage forms such as capsules, with limited light transmittance, e.g. to protect light-unstable active ingredients is often a balancing act between opacity and mechanical strength and stability of the capsule shell.

The inventors have now identified the concentration range and type of calcium carbonate that provides a good balance to achieve both good opacifying effect and mechanical strength It is to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the term "one or more", such as one or more members of a group of members, is clear per se, by means of further exemplification, the term encompasses inter alia a reference to any of said members, or to any two or more of said members, such as, e.g., any ≥3, ≥4, ≥5, ≥6 or ≥7 etc. of said members, and up to all said members.

The expression "low light transmittance" when used in combination with capsules or capsule formulations refers to capsules or capsule formulations that allow limited light transmittance and hence are to some extent capable of blocking light (e.g. natural or artificial) from entering into the cavity of the capsule body comprising the active ingredient. For a capsule comprising 10 wt. % precipitated $CaCO_3$ in its shell, typically an opacity coefficient of about 20% or more is envisaged, such as 25% or more, or 35% or more. Alternatively, the light transmittance coefficient can be indicated and implies the amount of light that is allowed to enter through the capsule shell. Typically a transmittance at 650 nm of below 35% is envisaged, preferably of below 25%, such as about 20% or less, or about 10% or less. For a capsule comprising 5 wt. % precipitated $CaCO_3$ in its shell, typically an opacity coefficient of about 15% or more is envisaged. Alternatively, the light transmittance coefficient can be indicated and implies the amount of light that is allowed to enter through the capsule shell. Typically a transmittance at 650 nm of below 55% is envisaged.

The opacity and transmittance of the capsules of the invention depend on the type of film forming polymer used and on the concentration of $CaCO_3$ used. As an exemplary guidance:
  when the capsule is an HPMC capsule having a calcium carbonate concentration of about 5 or 10%, it typically will have an opacity coefficient of 20% or higher. An HPMC capsule with 5% $CaCO_3$ will typically have a light transmittance at 650 nm of 35% or lower, while an HPMC capsule having about 10% $CaCO_3$ typically will have a light transmittance at 650 nm of 10% or lower;
  when the capsule is an HGC capsule having a calcium carbonate concentration of about 5 or 10%, it typically will have an opacity coefficient of 17% or higher. An HGC capsule with 10% $CaCO_3$ will typically have a light transmittance at 650 nm of 30% or lower, while an HGC capsule having about 5% $CaCO_3$ typically will have a light transmittance at 650 nm of 55% or lower;
  these values being determined on the average capsule wall thickness of standard capsules, i.e. of about 100 μm.

There are several methods for measuring particle size and particle size distribution. Some of them are based on light, other on ultrasound, or electric field, or gravity, or centrifugation.

In all methods the size is an indirect measure, obtained by a model that transforms, in abstract way, the real particle shape into a simple and standardized shape, like a sphere (the most usual) or a cuboid (when minimum bounding box is used), where the size parameter (ex. diameter of sphere) makes sense. Exception is the mathematical morphology approach, where no shape hypothesis is necessary.

Definition of the particle size for an ensemble (collection) of particles presents another problem. Real systems are practically always polydisperse, which means that the particles in an ensemble have different sizes. The notion of particle size distribution reflects this polydispersity. There is often a need for a certain average particle size for the ensemble of particles.

The term "D50 average particle size", or "Dv50", or volume basis median particle size indicates that in the particle mixture, the diameter of 50% (on the total mass) of the particles is smaller than, and the diameter of the other 50% (on the total mass) of the particles is larger than the indicated D50 average size. Typical measurement techniques are sieve analysis, direct imaging and laser diffraction known in the art.

The term "D4,3 average diameter size" or mean diameter over volume (also called the DeBroukere mean, following the conventions from ref. 2, American Society of Testing and Materials (ASTM) E 799), is the mean particle size based on the volume distribution and implies that the volume mean is used to define the central point of size distribution, although the median is more frequently used than the mean when using this technique. The values for D[4,3] are strongly impacted by the presence of aggregates which are not easily broken during measurement causing strong variation in measured particles size in the larger particles range. The equation is as follows:

$$D[3,4] = \frac{\sum_{i}^{n} D_i^4 v_i}{\sum_{i}^{n} D_i^3 v_i}$$

The term "particle size distribution", reflects the width or breadth of the distribution or particle sizes. Several calculations are used to describe the width of distribution but the most common calculations are standard deviation and variance.

The term "particle size span", indicates the broadness of particle size distribution and follows the equation: Span=(Dv0.9–Dv0.1)/Dv0.5, wherein Dv0.9 (D90), Dv0.1 (D10) and Dv0.5 (D50) represent the size at which respectively 90%, 10% and 50% of the particles are below said size, as e.g. measured by laser diffraction.

The term "high shear mixing" encompasses any type of high shear mixing at a speed of at least 15000 rpm, preferably at least 20000 rpm for at least 4 minutes. As a non-limiting example one can use the IKA Ultra Turraxx T25 mixer. The concentration of the dispersion is preferably at least 15 wt %, preferably above 20 wt %.

All documents cited in the present specification are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

The film-forming agent referred to herein can by any type of film-forming agent. Particularly envisaged film-forming agents are gelatin, polysaccharides, modified starches, or synthetic polymers. Non-limiting examples thereof include generally known agents, for example: cellulose based polymers such as methyl cellulose, ethyl cellulose, methylhydroxyethyl cellulose, hydroxypropyl cellulose, hydroxypropylmethyl cellulose, hydroxypropylmethylcellulose phthalate, hydroxypropylmethylcellulose acetate succinate, carboxymethylethylcellulose, and the like, polysaccharides such as pullulan, carrageenan, gellan, alginates, and the like; or gelatin; synthetic polymers such as polyvinyl alcohol, polyvinylacetal diethylamino acetate, aminoalkylmethacrylate copolymer E (sold under the trademark EUDRAGIT-E—Rohm Pharma Co. Ltd.), polyvinylpyrolidone, and the like; (meth)acrylate based polymers such as ethyl acrylate-methyl methacrylate copolymer suspensions (sold under the trademark EUDRAGIT NE (commercial name), Rohm Pharma Co. Ltd.), and the like; acrylate based polymers such as methacrylate copolymer L (sold under the trademark EUDRAGIT L—Rohm Pharma Co. Ltd.), methacrylate copolymer LD (sold under the trademark EUDRAGIT L-30D55—Rohm Pharma Co. Ltd.), and the like; as well as any combination thereof.

Gelatin, pullulan and cellulose based polymers are preferred. Of said cellulose based polymers, methylhydroxyethylcellulose, hydroxypropylcellulose, hydroxypropylmethylcellulose, and hydroxypropylmethylcellulose acetate succinate are more preferably used.

In addition to the film-forming agent(s), other additives can be added such as plasticizers, colorants, solvents, solvent aids, dispersants, solubilizers, stabilizers, correctives, sweeteners, adsorbents, absorbents, adherents, antioxidants, antiseptics, preservatives, desiccants, flavors, perfumes, pH adjusters, binders, lubricants, humectants, disintegrating agents, and/or release-controlling agents known in the art.

Adding additives such as dispersants (e.g. (iota-)carrageenan, sodium lauryl sulfate, sorbitan, or lecithin) can be beneficial.

When hard capsule shells are envisaged, said capsule shells may optionally further include other minor components conventionally used in capsules or that are used in the aqueous composition for dipping and that remain as part of the finished capsule. Examples of such materials include surfactants, de-foaming aids, anti-oxidants, viscosity modifiers, gelling agents, gelling aids, lubricants and plasticizers.

So called "setting systems" comprising gelling agents and/or gelling aids are conventionally relied upon in the manufacture of hard capsule shells by non-thermogelling dip-molding processes to confer an appropriate setting ability with cooling to film-forming polymers (like pullulan, HPMC or starch derivatives) that in these conditions have per se poor gelling properties. The setting system makes the aqueous composition to set on the dipped pins, thus enabling capsules production and assuring a uniform capsule shell thickness.

Such gelling agents and aids are well known in the art. Depending on the film-forming polymers to be used in the capsule shell manufacturing we refer to for example to U.S. Pat. No. 5,264,223 and EP714656 (discussing HPMC capsules), EP1117736 (discussing starch derivatives capsules); WO2005105051 and EP1072633 (discussing pullulan capsules).

In one embodiment, the setting system of the invention comprises one or more gelling agents. In one embodiment, the setting system of the invention comprises one or more gelling agents and one or more gelling aids, also known as co-gelling agents.

In one embodiment, the one or more gelling agents are selected from the group consisting of alginates, agar gum, guar gum, locust bean gum (carob), carrageenan (preferably kappa, lambda, and/or iota), tara gum, arabic gum, ghatti gum, khaya grandifolia gum, tragacanth gum, karaya gum, pectin, arabian (araban), xanthan, low and high acyl gellan gum, starch, konjac mannan, galactomannan, funoran, acetan, welan, rhamsan, furcelleran, succinoglycan, scleroglycan, schizophyllan, tamarind gum, curdlan, dextran and mixtures thereof. Preferably, the one or more gelling agents are selected from the group consisting of carrageenans (preferably kappa and/or iota, more preferably kappa-carrageenans), gellan gum and mixtures thereof. In one embodiment, the one or more gelling agents comprise, preferably consist of carrageenans (preferably kappa and/or iota, more preferably kappa-carrageenans). In one embodiment, the one or more gelling agents comprise, preferably consist of gellan gum.

In one embodiment, the one or more gelling agents comprise a combination of two or more of the agents listed above. In one embodiment, the one or more gelling agents comprise, preferably consist of a combination of xanthan and locust bean gum. In one embodiment, the one or more gelling agents comprise, preferably consist of a combination of xanthan with konjac mannan.

In one embodiment, the one or more gelling aids (also known as co-gelling agents) are cations. In one embodiment, the one or more gelling aids are selected from the group consisting of: $K^+$, $Li^+$, $Na^+$, $NH_4^+$, $Ca^{2+}$, $Mg^{2+}$ and mixtures thereof. Preferably, the one or more gelling aids are selected from the group consisting of: $K^+$, $NH_4^+$, $Ca^{2+}$ and mixtures thereof. The cations can be added to the setting system in the form of a pharmaceutically or food acceptable water soluble salt (e.g. chloride, acetate, citrate or phosphate).

In one embodiment, the setting system of the invention comprises one or more gelling agents selected from the group consisting of: carrageenans (preferably kappa and/or iota, more preferably at least kappa-carrageenans), gellan and mixtures thereof; and one or more pharmaceutically or food acceptable water soluble salts of $K^+$, $NH_4^+$, $Ca^{2+}$ and mixtures thereof.

In one embodiment, the aqueous composition of the invention contains one or more gelling agents as defined above in an amount suitable to obtain a hard capsule shell as defined below containing between about 0.01 and 3.0%, by weight, preferably between about 0.03 and 1.0%, by weight, preferably between about 0.1% and 0.5% by weight of such gelling agent(s) over the weight of the shell. Exemplary suitable gelling agents' amounts are readily available to a skilled person in the field of hard capsules manufacturing. For example, it is commonly accepted that hard capsule shells containing a "target" amount of gelling agents falling within the ranges identified above can be obtained via a dip-molding process by using aqueous compositions containing about ¼ (i.e. 25%) of that target amount (expressed as % by weight over the weight of the composition).

In one embodiment, the aqueous composition of the invention contains one or more gelling aids as defined above in an amount suitable to obtain a hard capsule shell as defined below containing about less than 3%, preferably about less than 2.0%, more preferably between about 0.5% to 2.0%, even more preferably between about 1.0% and 2.0% by weight of such one or more gelling aids over the weight of the shell. In case the gelling aids are cations, the above ranges are expressed as weight of the pharmaceutically or food acceptable water soluble salts containing the cation(s) over the weight of the shell. Exemplary suitable gelling aids amounts are readily available to a skilled person in the field of hard capsules manufacturing. For example, it is commonly accepted that when water is about 75% by weight over the weight of the aqueous composition, hard capsule shells containing a "target" amount of gelling aids can be obtained via a dip-molding process by using aqueous compositions containing about ¼ (i.e. 25%) of that target amount (expressed as % by weight over the weight of the composition).

The hard capsule shells can also contain residual water. Typically such shells comprise, for example, less than 25 wt %, preferably less than 20 wt %, more preferably from 0 wt % to 14 wt %, even more preferably from greater than 1 wt % to less than 10 wt %, and more preferably from 2 wt % to 7 wt % water by weight.

Although any active ingredient selected from active pharmaceutical ingredients, nutritional supplements, nutraceuticals, vitamins, minerals, cosmetics, health foods, or the like can be encapsulated in the capsule formulation of the present invention, light-unstable or light-sensitive ingredients are particularly suited. Non-limiting light-unstable medicaments that can be filled in the capsules to obtain effective light shielding are: dihydropyridine derivatives (e.g., nifedipine), antiviral HIV protease inhibitors (e.g., Ritonavir, Saquinavir), therapeutic agents for hyperlipidemia (e.g., clofibrate), iodine compounds (e.g., sodium iopodate, sodium iodide), polyunsaturated fatty acid derivatives (e.g., ethyl eicosapentaenoic acid (EPA), docosahexaenoic acid (DHA)), carotenoids (e.g., lycopene, bixin, β-carotene, xanthophyll, lutein), ubiquinones (coenzyme Q)(e.g., ubidecarenone used as a metabolizable cardiac stimulant), various vitamin derivatives, as well as indomethacin, colchicine, diazepam, syrosingopine, norethisterone, piretanide, propericyazine, perphenazine, mequitazine, medazepam, menatetrenone, indenolol hydrochloride, reserpine, sofalcone, bromocriptine mesilate, bufetolol hydrochloride and oprenolol hydrochloride when they are filled into the capsule formulation of the present invention. Among vitamin derivatives, fat-soluble ones are preferred for use. Examples include vitamin A derivatives (e.g., tretinoin, liver oil, retinol palmitate), vitamin A analogs (e.g., etretinate), vitamin D derivatives, vitamin E derivatives (e.g., tocopherol nicotinate, tocopherol acetate, tocopherol calcium succinate), and vitamin K derivatives (e.g., phytonadione (vitamin K1), menaquinone (vitamin K2), menadione (vitamin K3), menatetrenone, phytonadione).

A medicament as an active ingredient can be filled into the capsules of the present invention, either alone or in combination with any base or carrier, additive, or excipient. Any type of base or carrier, either fat-soluble or water-soluble, can be used as long as it does not impair the medicament's activity and does not affect various physical properties of the capsule shell, such as strength, gas permeability, and disintegration or dissolution profiles. Likewise, the base per se may be in a liquid or solid state at normal temperature as long as it can be filled into capsules with the help of heating or dilution with other solvents, etc. Examples of such a base include vegetable oils (e.g., soybean oil, sesame oil, cottonseed oil, olive oil), fatty acid glycerides (e.g., medium chain triglycerides), propylene glycol, propylene glycol fatty acid esters, polyethylene glycol, polyvinylpyrrolidone, triacetin, liquid paraffin, polyoxyethylene sorbitan fatty acid esters, sucrose fatty acid esters, ethanol and purified water, which may be used alone or in combination. Bases preferred for dissolving fat-soluble medicaments such as vitamins A, D, E and K are vegetable oils or fatty acid glycerides, with medium chain triglycerides being particularly preferred. In the case of using a water-soluble base, it is preferable to provide a protection layer between the shell layer and the medicament layer or a crystallization inhibitor in consideration of influences on the capsule shell.

A medicament to be filled into the capsule shell of the present invention is preferably exemplified by, but not limited to, those in a liquid form or those dissolved, suspended or emulsified in such a base as listed above. The medicament may also be in a solid form (e.g., powders, granules) or in a semi-solid form (e.g., creams or gels).

The invention hence provides for a capsule formulation for forming capsules with reduced light transmittance (also called opaque capsules) comprising:
    a film forming agent as defined herein; and
    an opacifying agent in the form of calcium carbonate in an amount of between 3 and 10 wt % based on dry weight of the capsule forming formulation. Preferably, said $CaCO_3$ is present in an amount of between 4 and 8% based on dry weight of the final capsule forming formulation, more preferably in an amount of between 4.5 and 6.5 wt % based on dry weight of the final capsule forming formulation.

As will become clear from the examples section, the amount and particle size of the calcium carbonate as well as the type of $CaCO_3$ influences the balance between opacity and mechanical strength of the films and capsules envisaged herein.

The inventors have found that a median particle size (Dv50) of between 0.2 and 2.0 µm and/or a D4,3 particle size of about 10 or less is particularly advantageous for forming such films and capsules.

The average particle size can be expressed as a "D50" (Dv50) median particle size of between 0.2 to 2 µm, such as between 0.5 and 1.5 µm, more preferably of between 0.3 to 1.2 µm, more preferably of between 0.4 to 1.1 µm, such as about 1 µm.

Alternatively, the particles can have a "D4,3" particle size of about 10 µm or less, more preferably of about 8 µm or less, such as about 6 µm or less, or about 4 µm or less, more particularly of between 1 and 10 µm, or between 1 and 8 µm, preferably of between 2 and 6 µm, more preferably of about 4 µm, e.g. between 3.5 and 4.5 µm.

Preferably, said calcium carbonate has a substantially round/prismatic particle shape. In a particular embodiment, the calcium carbonate encompasses small uniform round or prismatic particles Typically, the particle size span of the $CaCO_3$ particles as defined above is as low as possible. Preferably, said span is below 10, preferably below 8, more preferably below 6.

In a preferred embodiment, the $CaCO_3$ is precipitated, i.e. is prepared from calcium oxide (CaO—lime), whereto water is added to give calcium hydroxide. Subsequently carbon dioxide is passed through this solution to precipitate the desired calcium carbonate, in the industry as precipitated calcium carbonate (PCC). PCC is available in numerous crystal morphologies and sizes, which can be tailored to optimize performance in a specific application. The calcium oxide used as starting material for the precipitation process can be obtained through the milk of lime process, which encompasses crushing of high purity calcium carbonate rock into small particles or powder suitable for processing, heating the latter to about 1000° C., thereby taking the calcium carbonate apart into calcium oxide (CaO) and carbon dioxide ($CO_2$) which can be captured and reused in the precipitation process above.

In a preferred embodiment, said PCC has a median particle size of between 0.2 and 2.0 µm or a. D4,3 particle size of about 10 µm or less. Alternatively, the average particle size of PCC can be expressed as a "D50" (Dv50) median particle size of between 0.2 to 2 µm, such as between 0.5 and 1.5 µm, more preferably of between 0.3 to 1.2 µm, more preferably of between 0.4 to 1.1 µm, such as about 1 µm.

The invention hence provides for a method of preparing a film-forming composition with opacifying capacities comprising the steps of:
   a) preparing an aqueous dispersion of calcium carbonate opacifier through mixing;
   b) preparing a film-forming formulation comprising one or more film-forming agent selected from the group of: gelatin, polysaccharides, modified starches, (meth)acrylate based polymers, or synthetic polymers or a combination thereof;
   c) adding the aqueous dispersion of step a) to the solution of step b); and
   d) mixing the resulting dispersion of step c), thereby obtaining the film forming composition, comprising between 3 and 10 wt %, preferably of between 4 and 8 wt %, more preferably of between 5 and 7 wt %, such as from 4.5 to 6.5 wt % CaCO3 based on final dry weight of the film-forming composition. In one embodiment, said film-forming composition comprises 15-25 wt % HPMC such as 20.5 wt % HPMC; or 25-35 wt %, such as about 31 wt % gelatin based on total dry weight of final capsule forming formulation.

In one embodiment, said film-forming composition comprises 15-25 wt % HPMC such as 20.5 wt % HPMC; or 25-35 wt %, such as about 31 wt % gelatin based on total dry weight of final capsule forming formulation.

In one embodiment, step c) is performed in two steps: c1) adding a part of the film-forming formulation of step b) to the dispersion of step a) to form a slurry and c2), adding said slurry to the remaining film forming formulation.

Preferably, said slurry is formed using high shear mixing such as mixing at a speed of at least 10000 rpm, such as e.g. 12000 rpm or more for at least 2 minutes.

In one embodiment, said mixing in step a) encompasses high shear mixing, such as mixing at a speed of at least 15000 rpm, preferably at least 20000 rpm for at least 4 minutes.

Without wanting to be bound to any theory, the high shear mixing can result in a better dispersion of the CaCO$_3$ in the film-forming composition, leading to increased mechanical strength.

In one embodiment, the opacifier is present in an amount of between 3-10 wt %, such as between 4 and 8 wt %, more preferably of between 5 and 7 wt % based on final dry weight of the film-forming composition.

The invention also provides in a method of making capsules comprising the steps of:

a) preparing a film forming composition as defined herein and b) producing a capsule e.g. by the conventional processes like extrusion moulding, injection moulding, casting or dip moulding. Typically, such a dip molding method comprises the steps of: dipping a mold pin in the film-forming composition at an adequate temperature to allow film-forming thereof on said dipping pin; ((hot)-air-)drying of the said film on the dipping pin; and removing the film-formed capsule half from said dipping pin.

The capsules obtained through the methods as described herein typically will have an opacity coefficient of about 20% or higher and/or a light transmittance at 650 nm of 35% or lower when e.g. a concentration of 10% w/w of precipitated calcium carbonate is used. When using a lower concentration of calcium carbonate such as about 5%, an opacity coefficient of about 17% or higher and/or a light transmittance at 650 nm of 55% or lower is reached. Said ranges are based on a capsule wall thickness of approximately 100 µm (e.g. from 90 µm to 110 µm) as is standardly used for commercial capsules.

Such capsules can of course be used for delivery of any type of ingredient but are particularly suitable for active ingredients that have limited light-stability. Examples of active ingredients can be active pharmaceutical ingredients, nutritional supplements, nutraceuticals, vitamins, minerals, cosmetics, health foods, or the like. Such an ingredient can be present in an amount of between 0.05 wt % to up to 100 wt %. Typically, the active ingredient can present in an amount ranging from about 0.5 wt % to about 90 wt % based on the total dry weight of said filling formulation, preferably from about 1 wt % to about 50 wt %, more preferably from about 5 wt % to about 30 wt % based on the total weight of said filling formulation.

In one embodiment, the capsules in which the opacifier is used are: HPMC-based capsules such as plant based capsules sold under the trademarks VEGICAPS, or VCAPS as described in U.S. Pat. No. 6,517,865; VCAPS Plus as described in U.S. Pat. No. 9,655,860; Pullulan-based capsules such as those described in U.S. Pat. No. 6,887,307; or enteric capsules such as VCAPS Enteric, described in WO2018/017799A1 and WO2013164121, the contents of which are hereby incorporated by reference. The preferred methods for producing such methods are also disclosed in said patents and hereby incorporated by reference.

The present invention is further illustrated in the following non-limiting examples.

EXAMPLES

Materials and Methods
Mechanical Strength Testing of Films

Film mechanical properties were determined by tensile tests performed according to ASTM D882-02 (using INSTRON 5965 tester) on the samples that were stored at 22° C. and 50% RH and 23% RH. Films were stored at these conditions for 7 days. For most tensile testing of materials, you will notice that in the initial portion of the test, the relationship between the applied force, or load, and the elongation the specimen exhibits is linear. In this linear region, the line obeys the relationship defined as "Hooke's Law" where the ratio of stress (a) to strain (E) is a constant, or according to Hooke's law:

$$\frac{\sigma}{\varepsilon} = E$$

"E" is the slope of the line in this region where stress (a) is proportional to strain (E) and is called the "Modulus of Elasticity" or "Young's Modulus".

Mechanical Strength of Capsules

Test capsules are prepared as outlined below from the different film-forming compositions using conventional dip mold technology, wherein size 0 capsules are produced, having a capsule side wall thickness of about 100 µm. The mechanical strength of the manufactured capsules was evaluated by the tube test method (internal impact method) In short, a weight of 100 g is dropped onto capsules (n=50) from a height of 8 cm and the number of broken capsules are counted and expressed as a percentage.

Capsules were stored at room temperature, at 2.5%, 10%, 23%, 33% and 45% relative humidity (RH) for 7 days. The measurements were done at room temperature.

Opacity Testing

Opacity was measured by a spectrophotometer (COLOREYE XTH Portable Spectrophotometer, X-Rite, Incorporated) using the phase-contrast imaging method. For the measurement of light transmittance, the film samples were placed in the light pathway in the ultraviolet-visible (UV-VIS) spectrophotometer, and the transmittance at 650 nm was recorded. Films were kept at room temperature.

For opacity testing, films of approximately about 100 µm thick were prepared from the different film-forming compositions as explained below. Such films correspond in terms of thickness to the side wall thickness of capsules ranging from 90-110 µm.

The term "opacity coefficient" as used herein corresponds to the Contrast Ratio Opacity (OP), i.e. the ratio between luminance or brightness measured against black and white background. OP measurements quantify how close to opaque a near-opaque material is.

The measurement is a two-part program metric where the Y (luminance or brightness) value is first measured on the sample backed by a black background, followed by a second measurement of the Y value of the sample backed by a white background. The resulting fraction is expressed as Y %, calculated as follows:

$$OP = Y_{black\ backing}/Y_{white\ backing} \times 100$$

Particles Size Measurement and Imaging

Particles size was determined using laser diffraction method (MASTERSIZER 2000 analyzer, Malvern). The measurements were done on dry powder that was dispersed using the air pressure of 2 bar.

Particles were imaged with a SEM.

High Shear Mixing

High shear mixing of the opacifying solution or dispersion was done using an ULTRA TURRAX T25 mixer (IKA) at a speed of 21000 rpm for at least 6 min. Concentration of the dispersion is at least 15 wt %, preferably above 20 wt %.

Example 1: Film-Forming Formulation Design $CaCO_3$ was tested for its ability to induce opacity and for its effect on the mechanical strength of the polymeric films formed. This was tested on both cellulose-based (HPMC) and gelatin-based films.

A dispersion of non-encapsulated CaCO3 is first prepared and added to the film-forming formulation. The same general procedure is used for gelatin and HPMC formulations.

In short, 60 g of water was added to 22.45 g of precipitated $CaCO_3$ (PCC) and the mixture was homogenized with high shear mixing (e.g. high shear mixing at 21000 rpm (ULTRA TURRAX mixer, IKA) for 3×2 minutes with 30 sec pause between each mixing).

Subsequently a part of (e.g. 20 g) of the liquid film-forming HPMC or gelatin formulation, comprising 20.5 wt % HPMC in water or 31 wt % gelatin in water is added and mixed into the dispersion under stirring at 12000 rpm (e.g. Silverson apparatus), during e.g. 3 minutes, thereby forming a slurry. Said slurry is then mixed with the remaining part of the film-forming formulation, thereby forming the film-forming composition resulting in a 10 wt % $CaCO_3$ concentration based on the final dry weight of said film-forming composition.

Encapsulated $CaCO_3$ (10 wt % based on total dry weight of final capsule forming formulation) was dispersed in water by stirring with a helix mixer for about 45 minutes. The required quantity of the resulting dispersion was added to the liquid film-forming HPMC or gelatin formulation, comprising 20.5 wt % HPMC in water or 31 wt % gelatin in water based on total dry weight of final capsule forming formulation, and mixed.

HPMC-based films were prepared as follows: glass plates were kept at 60° C., the film-forming composition comprising the different amounts of $CaCO_3$ was kept at 28° C. and films were casted in a warm reservoir (40-50° C.) using e.g. a TLC plate coater, hand operated (sold under the trademark CAMAG, Muttenz, CH). The films were then left to dry at 60° C. for about 1 hour and kept overnight at 22° C., at a RH of 50%.

Gelatin films were formed as follows: glass plates were kept at 60° C., the film-forming solution comprising the different amounts of $CaCO_3$ was kept at 55° C. and films were casted in a warm reservoir (about 60° C.) using e.g. a TLC plate coater (sold under the trademark CAMAG, Muttenz, CH). The films were then left to dry overnight at 22° C., at a RH of 50%.

The results of tests on HPMC and HGC films are depicted in Table 1 below:

| Polymer | Opacifier | wt %* | Reported particle size (µm) | Opacity (%) | Transmittance at 650 nm (%) | Mechanical properties |
|---|---|---|---|---|---|---|
| HPMC | $TiO_2$ | 2.0 | 0.1-1 | 61.4 | 0.7 | 5 |
| HPMC | PCC | 10 | 0.7 | 32.8 | 7.9 | 3 |
| HPMC | Encapsulated agglomerated $CaCO_3$ | 10 | 3-5 | 37.05 | 9.3 | 1 |
| HGC | TiO2 | 2.0 | 0.1-1 | 61.4 | 0.7 | 5 |
| HGC | PCC | 10 | 0.7 | 23.88 | 27.5 | 3 |
| HGC | Encapsulated agglomerated $CaCO_3$ | 10 | 3-5 | 32.1 | 28.8 | 1 |
| HGC | Ground $CaCO_3$ | 10 | 3.8 | 21.7 | 19.8 | 1 |

*based on dry weight of total final capsule forming formulation

The score of 0 to 5 indicates the mechanical properties, 5 being the highest score, 0 being the lowest score in terms of mechanical properties.

HPMC stands for hydroxypropylmethylcellulose

HGC stands for hard gelatin capsule

The above results indicated that calcium carbonate shows potential as an opacifier retaining acceptable mechanical strength, although some differences were observed between $CaCO_3$ having different particle size. Particularly interesting is that the encapsulated and ground $CaCO_3$ result in less mechanical strength of the films.

In all further experiments, the term "precipitated $CaCO_3$" refers to PCC as indicated in Table 1.

Figure 1A:
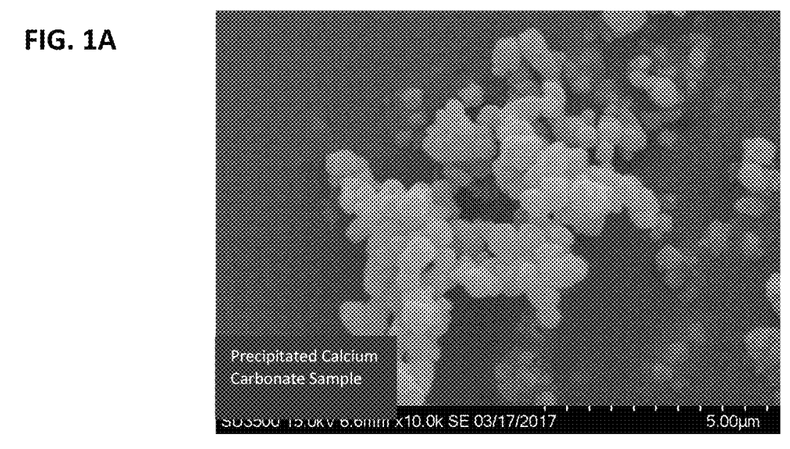
FIG. 1A and FIG. 1B are scanning electron microscope (SEM) images of different types of $CaCO_3$ particles: A) precipitated $CaCO_3$ presenting small uniform round/prismatic particles; B) encapsulated $CaCO_3$ showing agglomerated granules forming large particles (up to 100 μm).
Figure 1B:
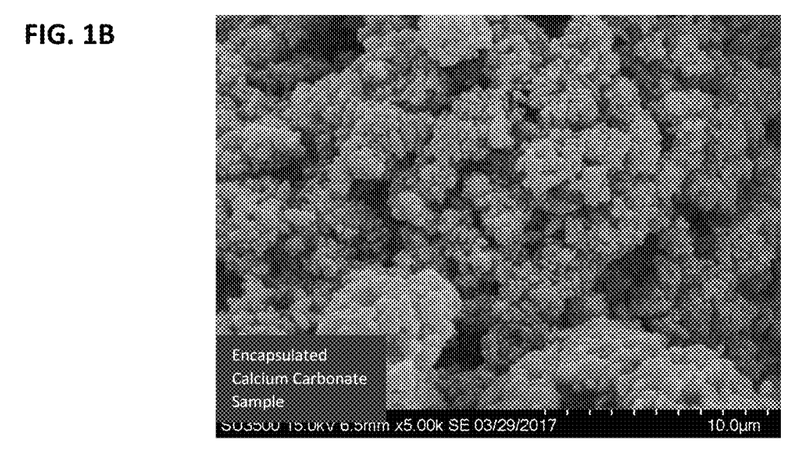

Using SEM imaging, the particle size and shape of the different $CaCO_3$ compositions were analysed. To this end, the particles were coated with metal and imaged using a scanning electron microscope known in the art. The scale bar is given in the images.

As follows from FIGS. 1A and 1B, the particle size and shape of the $CaCO_3$ compositions tested is quite different: FIG. 1B shows agglomerated granules of the encapsulated $CaCO_3$, forming large particles (up to 100 µm), while FIG. 1A shows much smaller particles of the PCC, having a small round/prismatic shape and being more uniform in particle shape and size distribution than the encapsulated $CaCO_3$.

Next, the particle size of the different $CaCO_3$ compositions was analyzed using a laser diffraction method as indicated above (cf. Table 2).

TABLE 2

| CaCO$_3$ | D50 (μm) | D4,3 (μm) | SEM remarks |
|---|---|---|---|
| PCC | 0.91 | 6.19 | Small, round/prismatic, uniform particles |
| encapsulated CaCO$_3$ | 9.9 | 33.9 | ~100 μm granules made of 1 μm particles |

Particle size and shape of precipitated and encapsulated CaCO$_3$

Example 2: Tests on HPMC Films and Capsules

Next, a study was done on the impact of different levels of calcium carbonate on the films and capsules properties.

For this, the same procedure as used for producing HPMC films according to example 1 was used, but with several calcium carbonate concentrations and types (PCC as in Table 1 or 2, or encapsulated CaCO$_3$). The following protocol was used to prepare the 10 wt % CaCO$_3$ in a 20.5 wt. % HPMC-based films:

| Step 1 | HPMC solution | |
|---|---|---|
| | HPMC | 202.05 g |
| | Water | 783.56 g |
| | (cc of HPMC | 20.5 wt %) |
| Step 2 | Dispersion preparation | |
| | CaCO$_3$ | 22.45 g |
| | Water | 60 g |
| | (cc of PCC | 27.2 wt %) |
| Step 3 | Slurry preparation | |
| | Dispersion from Step 2 | 82.45 g |
| | HPMC solution from Step 1 | 20 g |
| Step 4 | Final formulation | |
| | Polymer solution | 965.61 g |
| | slurry | 102.45 g |
| Result | 10 wt % CaCO$_3$ on 20.5 wt % HPMC capsule | |

In order to reach a film forming composition comprising 6.5 wt % of CaCO$_3$ based on the final dry weight of said film-forming composition, step 4 of the above protocol is as follows:

| Step 1 | HPMC solution | |
|---|---|---|
| | HPMC | 322.93 g |
| | Water | 1252.36 g |
| | (cc of HPMC | 20.5 wt %) |
| Step 2 | Dispersion preparation | |
| | CaCO$_3$ | 22.45 g |
| | Water | 60 g |
| | (cc of PCC | 27.2 wt %) |
| Step 3 | Slurry preparation | |
| | Dispersion from Step 2 | 82.45 g |
| | HPMC solution from Step 1 | 20 g |
| Step 4 | Final formulation | |
| | Polymer solution | 1555.29 g |
| | slurry | 102.45 g |
| Result | 6.5 wt % CaCO$_3$ on 20.5 wt % HPMC capsule | |

In order to reach a film forming composition comprising 5 wt % or 7.5 wt % of CaCO$_3$ based on the final dry weight of said film-forming composition, the above protocols can be adjusted by changing the relative amount of HPMC film-forming formulation vs. CaCO$_3$ dispersion.

The opacity and light transmittance of the different HPMC-based films were tested and the results are presented in Table 3 below.

TABLE 3 opacity and transmittance at 650 nm of HPMC films containing different CaCO$_3$ types at two concentrations compared to transparent and films opacified with TiO2.

| | Transparent | 2% TiO$_2$ | 5% PCC | 10% PCC | 5% Encapsulated CaCO$_3$ | 10% Encapsulated CaCO$_3$ |
|---|---|---|---|---|---|---|
| Opacity (%) | 15.09 | 63.09 | 23.3 | 32.8 | 25.07 | 37.05 |
| Transmittance at 650 nm (%) | 90.1 | 0.7 | 26.6 | 7.9 | 27.3 | 9.3 |

Also the tensile properties of said films were tested using the Instron device according to ASTM D882-02. As shown in Table 4, the comparison between HPMC capsules comprising 5 or 10 wt % precipitated or encapsulated CaCO$_3$ does not show a marked difference in tensile properties because the HPMC films are by nature difficult to deform.

TABLE 4

Tensile properties of HPMC films with different CaCO$_3$ concentrations

| | | Transparent | 2% TiO$_2$ | 5% PCC | 10% PCC | 5% Encapsulated CaCO$_3$ | 10% Encapsulated CaCO$_3$ |
|---|---|---|---|---|---|---|---|
| 50% RH | Young's modulus (MPa)(stdev) | 1800 (98) | 1990 (95) | 1862 (70) | 1940 (80) | 1803 (131.5) | 1907 (158) |
| | % deformation | 12.5 | 13.9 | 9.06 | 7.07 | 11 | 7.8 |

TABLE 4-continued

Tensile properties of HPMC films with different CaCO3 concentrations

|     |                                 | Transparent  | 2% TiO2      | 5% PCC       | 10% PCC      | 5% Encapsulated CaCO3 | 10% Encapsulated CaCO3 |
| --- | ------------------------------- | ------------ | ------------ | ------------ | ------------ | --------------------- | ---------------------- |
|     | (stdev)                         | 3.3          | 2.9          | 1.16         | 1.1          | 2.9                   | 1.5                    |
|     | Max % deform.                   | 18.8         | 20           | 11.73        | 9.8          | 14.7                  | 11.12                  |
| 23% RH | Young modulus (MPa)(stdev)   | 1852 (175)   | 2030 (132)   | 2081 (89.9)  | 2033 (113)   | 2056 (85.9)           | 2103 (137)             |
|     | % deformation (stdev)           | 13.25        | 12.93        | 9.6          | 7.8          | 10.8                  | 7.2                    |
|     |                                 | 3            | 2.6          | 1.95         | 1.8          | 2.9                   | 1.1                    |
|     | max % deform.                   | 19.8         | 17.4         | 12.8         | 11.2         | 16.9                  | 9.93                   |

Next, HPMC capsules were formed using a conventional mold-dipping technique summarized in here: The dip pins of size 0 are pre-heated at about 73° C., while the dipping composition is maintained at 32° C. Capsules of size 0 are manufactured by the conventional dipping process, with pre-heated pins.

After the dipping, the capsules are dried with hot air at 60° C. and 40% RH for 30 minutes and then at about 22° C. and 50% RH, for about 20 minutes.

The influence of precipitated $CaCO_3$ and encapsulated $CaCO_3$ on mechanical strength when used at 10 wt % in HPMC capsules was compared and from the tube test evaluation it becomes clear that the precipitated $CaCO_3$ is better for mechanical performance (less broken capsules, cf. Table 5).

TABLE 5 comparison of effect of precipitated vs encapsulated $CaCO_3$ on mechanical strength of HPMC-based capsules:

| 10 wt % CaCO3    | % RH | Total broken capsules (%) |
| ---------------- | ---- | ------------------------- |
| encapsulated CaCO3 | 10 | 100                       |
|                  | 23   | 88.24                     |
|                  | 33   | 47.06                     |
|                  | 45   | 0                         |
| PCC              | 10   | 96                        |
|                  | 23   | 46                        |
|                  | 33   | 10                        |
|                  | 45   | 0                         |

The mechanical strength of HPMC-based capsules formed using a film-forming composition comprising 10 wt %, 7.5 wt % or 6.5 wt % precipitated $CaCO_3$ (prepared according to the protocols of Examples 1 and 2) was subsequently tested using the tube test (internal impact test) as indicated above (Table 6).

TABLE 6 comparison of effect of different $CaCO_3$ concentrations on mechanical strength of HPMC-based capsules:

| wt % PCC | % RH | Total broken capsules (%) |
| -------- | ---- | ------------------------- |
| 10%      | 10   | 96                        |
|          | 23   | 46                        |
|          | 33   | 10                        |
|          | 45   | 0                         |
| 7.5%     | 2.5  | 94                        |
|          | 10   | 82                        |
|          | 23   | 31                        |
|          | 33   | 16                        |
|          | 45   | 0                         |
| 6.5%     | 2.5  | 90                        |
|          | 10   | 68                        |
|          | 23   | 18                        |
|          | 33   | 6                         |
|          | 45   | 2                         |
| 5.5%     | 2.5  | 70                        |
|          | 10   | 62                        |
|          | 23   | 8                         |
|          | 33   | 4                         |
|          | 45   | 2                         |

Based on said results, we can summarize the conditions for calcium carbonate to be effective in HPMC capsules into a concentration range of between 3 and 10 wt % of precipitated $CaCO_3$, which results in capsules with acceptable opacity and mechanical strength.

Example 3: Test on Gelatin Films

The film-forming composition and method from Example 1 was used to produce gelatin films.

| Step 1 | gelatin solution (HGC melt preparation) |             |
| ------ | --------------------------------------- | ----------- |
|        | gelatin                                 | 322.94 g    |
|        | Water                                   | 718.79 g    |
|        | (cc of gelatin)                         | 31 wt %     |
| Step 2 | Dispersion preparation                  |             |
|        | CaCO3                                   | 22.45 g     |
|        | Water                                   | 60 g        |
|        | (cc of CaCO3)                           | 27.2 wt %   |
| Step 3 | Slurry preparation                      |             |
|        | Dispersion from Step 2                  | 82.45 g     |
|        | gelatin solution from Step 1            | 20 g        |
| Step 4 | Coloring the formulation                |             |
|        | Polymer solution                        | 1021.71     |
|        | slurry                                  | 102.45      |
| Result | 6.5 wt % CaCO3 on 30.1 wt % gelatin capsule |         |

Opacity and light transmittance at 650 nm were tested as explained above and the results are outlined in Table 7 below. Comparable results are obtained for PCC (Table 1 or 2) and encapsulated $CaCO_3$.

TABLE 7 opacity and transmittance at 650 nm of gelatin-based films

|  | Transparent | 2% TiO$_2$ | 5% precip. CaCO$_3$ | 10% precip. CaCO$_3$ | 5% Encapsulated CaCO$_3$ | 10% Encapsulated CaCO$_3$ |
|---|---|---|---|---|---|---|
| Opacity (%) | 15.83 | 62.4 | 18.96 | 23.88 | 24.15 | 32.1 |
| Transmittance at 650 nm (%) | 82.2 | 1.7 | 49.2 | 27.5 | 48.5 | 28.8 |

Tensile tests on films were done as explained above for the HPMC films and show that films with precipitated CaCO$_3$ can be deformed more than films containing encapsulated CaCO$_3$ (cf. Table 8).

TABLE 8

Tensile properties of gelatin-based films with different CaCO$_3$ concentrations

| | | Transparent | 2% TiO$_2$ | 5% precip. CaCO$_3$ | 10% precip. CaCO$_3$ | 5% Encapsulated CaCO$_3$ | 10% Encapsulated CaCO$_3$ |
|---|---|---|---|---|---|---|---|
| 50% RH | Young's modulus (MPa)(stdev) | 2359 (123) | 3032 (127) | 2483 (145.5) | 2507 (145.3) | 2510.7 (91.2) | 2600 (125) |
| | % deformation (stdev) | 24.5 | 12.44 | 15.9 | 13.3 | 11.8 | 11.5 |
| | | 10.9 | 5 | 6.7 | 4.5 | 5 | 2.1 |
| | Max % def | 47.3 | 27.28 | 30.4 | 21.4 | 24.6 | 15.1 |
| 23% RH | Young modulus (MPa)(stdev) | 2398 (141) | 3112 (122) | 2784 (127) | 2861 (126) | 2521 (112.7) | 2601 (151) |
| | % deformation (stdev) | 41.8 | 23 | 14.8 | 12.9 | 12.8 | 14.86 |
| | | 11.2 | 9.4 | 5.9 | 6.3 | 5.8 | 6.1 |
| | max % def | 58.6 | 44.44 | 27.4 | 28.8 | 28.6 | 27.4 |

This film-forming composition can also be used to produce gelatin-based capsules through conventional mold dipping. In short, by dipping stainless steel mold pins at room temperature (at about 22° C.) into a hot liquid gelatin solution (e.g. about 45° C.), a film of controlled dimensions is formed on the mold. After drying, this results in capsule halves with shell wall thickness of about 100 μm.

Example 4: Industrial Scale Test

Using the same film-forming composition as in Example 2, 550,000 HPMC capsules size 0 and 625,000 HPMC capsules size 1, were manufactured with a good quality and acceptable opacity. Overall trial outcomes are hence very positive.

We claim:

1. A hard capsule shell comprising:
   a film-forming agent, wherein the film-forming agent is gelatin, or pullulan, or a cellulose based polymer, or any combination thereof; and
   an opacifying agent in the form of precipitated calcium carbonate having a median particle diameter D50 of between 0.2 μm and 2.0 μm as measured by laser diffraction, and present in an amount of 3 wt % to 10 wt % based on dry weight of the capsule shell.

2. The hard capsule shell of claim 1, wherein the opacifying agent is present in an amount of 8 wt % to 10 wt % based on dry weight of the capsule shell.

3. The hard capsule shell of claim 1, wherein the film-forming agent is methylcellulose, hydroxymethylcellulose, hydroxypropylcellulose, methylhydroxyethylcellulose, hydroxypropylmethylcellulose (HPMC), hydroxypropylmethylcellulose phthalate, hydroxypropylmethylcellulose acetate succinate (HPMCAS), carboxymethylethylcellulose, or any combination thereof.

4. The hard capsule shell of claim 1, wherein the film-forming agent is gelatin, or pullulan, or HPMC.

5. The hard capsule shell of claim 1, wherein the film-forming agent is HPMC or gelatin.

6. The hard capsule shell of claim 1, wherein the film-forming agent is HPMC.

7. The hard capsule shell of claim 1, wherein the film-forming agent is gelatin.

8. The hard capsule shell of claim 1, wherein the film-forming agent is pullulan.

9. The hard capsule shell of claim 1, further comprising an additive that is a gelling agent, a gelling aid, a viscosity modifier, a de-foaming aid, a plasticizer, a lubricant, a colorant, a solvent, a solvent aid, a surfactant, a dispersant, a solubilizer, a stabilizer, a sweetener, an adsorbent, an adherent, an antioxidant, an antiseptic, a preservative, a desiccant, a flavor, a perfume, a pH adjuster, a binder, a disintegrating agent, a release-controlling agent, or any combination thereof.

10. A method of producing the hard capsule shell of claim 1 using a dip coating process comprising:
    dipping a mold pin in a capsule-forming composition comprising the film forming agent and the opacifying agent to form a film on the mold pin;
    drying the film on the mold pin to form a hard capsule shell half; and
    removing the hard capsule shell half from the mold pin, wherein the hard capsule shell half exhibits reduced light transmittance.

11. The method of claim 10, wherein the hard capsule shell half comprises 8 wt % to 10 wt % of the opacifying agent based on final dry weight of the hard capsule shell half.

12. A method of preparing a hard capsule shell of claim 1, comprising the steps of:

a) preparing an aqueous dispersion of precipitated calcium carbonate opacifier through mixing;

b) preparing a film-forming formulation comprising one or more film-forming agents, wherein the film-forming agent is gelatin, or pullulan, or a cellulose based polymer, or any combination thereof;

c) adding the aqueous dispersion of step a) to the film-forming formulation of step b);

d) mixing the resulting dispersion of step c), thereby obtaining a film-forming composition comprising 3 wt % to 10 wt % of the precipitated calcium carbonate opacifier based on final dry weight of the film-forming composition; and e) producing a hard capsule shell from the film-forming composition by means of dip molding.

13. The method of claim 12, wherein the film-forming composition comprises 8 wt % to 10 wt % of the precipitated calcium carbonate opacifier based on final dry weight of the film-forming composition.

14. The method of claim 12, wherein step c) is performed in two steps, c1) and c2), wherein c1 comprises adding a part of the film-forming formulation of step b) to the dispersion of step a) to form a slurry and c2 comprises adding the slurry to the remaining film forming formulation.

15. The method of claim 12, wherein the film-forming agent is gelatin, or pullulan, or HPMCAS, or HPMC.

16. The method of claim 15, wherein the film-forming agent is gelatin or HPMC.

17. The method of claim 15, wherein the film-forming agent is gelatin.

18. The method of claim 15, wherein the film-forming agent is HPMC.

* * * * *